(12) United States Patent
Hassila et al.

(10) Patent No.: US 6,930,189 B2
(45) Date of Patent: Aug. 16, 2005

(54) CHIRAL LIGAND

(75) Inventors: Heikki Hassila, Ibaraki (JP); Takayuki Higashii, Ibaraki (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/724,731

(22) Filed: Dec. 2, 2003

(65) Prior Publication Data

US 2004/0110965 A1 Jun. 10, 2004

Related U.S. Application Data

(62) Division of application No. 10/097,009, filed on Mar. 14, 2002, now Pat. No. 6,762,306.

(30) Foreign Application Priority Data

Mar. 14, 2001 (JP) .................................... 2001-071784

(51) Int. Cl.$^7$ ............................................ C07D 205/04
(52) U.S. Cl. ..................................................... 548/950
(58) Field of Search ................................. 548/950, 953

(56) References Cited

U.S. PATENT DOCUMENTS 6,762,306 B2 * 7/2004 Hassila et al. .............. 548/950

OTHER PUBLICATIONS

Pasquier et al., Synthetic Letters, vol. 10. pp. 1162–1 164 (Oct. 1998).*
Pasquier et al., Organometallics, vol. 19, No. 26, pp. 5723–5732, (2000).
Pasquier et al., Synthetic Letters, vol. 10, pp. 1162–1164, (1998).
Aboulhoda et al., Tetrahedron: Asymmetry, vol. 5, No. 7, pp. 1321–1326, (1994).
Behnen et al., Tetrahedron: Asymmetry, vol. 4, No. 7, pp. 1413–1416, (1993).

* cited by examiner

*Primary Examiner*—Joseph K. McKane
*Assistant Examiner*—Janet L Coppins
(74) *Attorney, Agent, or Firm*—Birch, Stewart, Kolasch & Birch, LLP

(57) ABSTRACT

There is disclosed a chiral phosphine compound of formula (1):

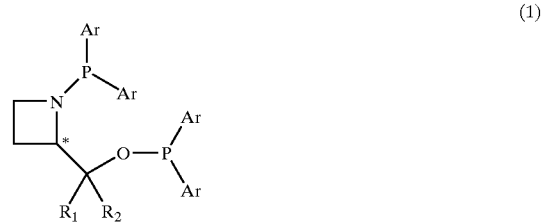

(1)

The chiral phosphine compound is suitably used to produce a transition metal complex that is useful as an asymmetric reaction catalyst.

2 Claims, No Drawings

CHIRAL LIGAND

This application is a Divisional of co-pending Application Ser. No. 10/097,009, filed on Mar. 14, 2002 now U.S. Pat. No. 6,762,306, and for which priority is claimed under 35 U.S.C. §120; and this application claims priority of Application No. 2001-071784 filed in Japan on Mar. 14, 2001 under 35 U.S.C. §119.

FIELD OF THE INVENTION

The present invention relates to a chiral transition metal complex, which is useful as a catalyst for converting a prochiral unsaturated organic compound to a corresponding asymmetric compound, and a process for producing the same.

BACKGROUND OF THE INVENTION

Martins et al. discloses an optically active transition metal complex catalyst having an aminophosphine-phosphinite ligand (Synlett., 1998, Vol. 10, pp1162), however, the catalyst was not always satisfactory in the asymmetric reaction of converting a carbonyl compound to a chiral alcohol compound.

Hence, a more effective catalyst that can be suitably used for industrial-scale production has been desired.

SUMMARY OF THE INVENTION

According to the present invention, an efficient catalyst for asymmetric production process is provided.

The present invention provides:

1. a chiral phosphine compound of formula (1):

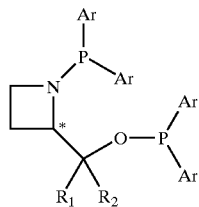

(1)

wherein $R_1$ and $R_2$ independently represent
an aryl or heteroaryl group, which may be substituted,
a saturated hydrocarbon group, which may be substituted, and
Ar group independently represents
an aryl or heteroaryl group, which may be substituted,
an aryloxy group, which may be substituted,
a saturated hydrocarbon group, which may be substituted,
or
Ar groups on the same phosphorus atom are bonded to form an arylene, heteroarylene or alkylene group, which may be substituted, and
* represents an asymmetric carbon atom;

2. a transition metal complex of a chiral phosphine compound of formula: (1) as defined above;

3. a process for producing a chiral phosphine compound of formula (1) as defined above, which comprises reacting an optically active azetidine alcohol compound of formula (2):

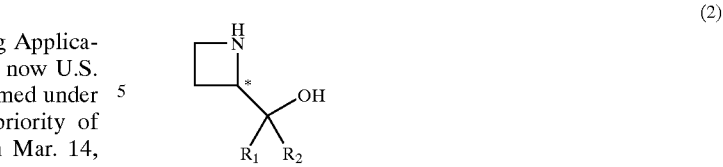

(2)

wherein $R_1$, $R_2$ and * represent the same as defined above, with a phosphine of formula (3):

$$X\text{—}P(Ar)_2 \qquad (3),$$

wherein X represents a leaving group (e.g. a halogen atom, or the like.)
Ar represents the same as defined above;

4. an optically active azetidine alcohol compound of formula (4):

(4)

wherein $R_1$ and $R_2$ independently represent
a saturated hydrocarbon group, which may be substituted, and
* represent the same as defined above; and 5. a process for producing an optically active organic compound, which comprises asymmetrically reducing a prochiral unsaturated compound with hydrogen in the presence of the transition metal complex of a compound of formula (1) as defined above.

DETAILED DESCRIPTION OF THE INVENTION

A description will be made to $R_1$, $R_2$ and Ar group of the chiral phosphine compound of formula (1), the transition metal complex of the chiral phosphine compound of formula (1), and the optically active azetidine alcohol of formula (2).

Examples of the heteroaryl or aryl group, which may be substituted include, for example, a (C6–C12) aryl group such as a phenyl group, tolyl group, naphthyl group, biphenyl group or the like, and a (C4–C5) heteroaryl group such as a furyl, thienyl or pyridyl group, or the like.

Examples of the saturated hydrocarbon group include, for example, linear, branched or cyclic alkyl group, which may be substituted.

Specific examples of the linear, branched or cyclic alkyl group include, for example, a linear, branched or cyclic (C1–C10) group such as a methyl group, ethyl group, n-propyl group, isopropyl group, n-butyl group, isobutyl group, t-butyl group, n-amyl group, neopentyl group, cyclopentyl group, n-hexyl group, cyclohexyl group, n-octyl group, n-nonyl group, mentyl group, 2,3,4-trimethyl-3-pentyl group, 2,4-dimethyl-3-pentyl group, or the like.

The aryl, heteroaryl, and saturated hydrocarbon groups may be substituted, for example with a halogen atom, an alkoxy group, an aryloxy group, an alkylthio group, an arythio group, a nitro group or a sulfonic group.

The aryl and heteroaryl groups may be substituted with an alkyl group such as the linear, branched or cyclic (C1–C10)

alkyl group as described above, and preferred alkyl groups include, a methyl group, an ethyl group, an isopropyl group, a n-butyl group, a t-butyl group, a n-amyl group, a n-hexyl group and the like.

Examples of the halogen atom are a fluorine atom, a chlorine atom, a bromine atom, and an iodine atom.

Examples of the alkoxyl group include, for example, a (C1–C4) alkoxy group such as methoxy group, ethoxy group, n-propoxy group, t-butoxy group or the like.

Examples of the alkylthio group include, for example, those comprised of the (C1–C10)alkyl group, as described above, and thio group, and specific examples thereof include, for example, n-propylthio group, t-butylthio group or the like.

Examples of the arylthio group include, for example, those comprised of the (C6–C12) aryl group, as described above, and a thio group, and specific examples thereof include, for example, a phenylthio group or the like.

Examples of the aryloxy group, which may be present on the aryl, heteroaryl, and saturated hydrocarbon groups, for example, those comprised of the (C6–C12) aryl group, as described above, and an oxy group, and specific examples thereof include, for example, a phenoxy group or the like.

The saturated hydrocarbon groups may also be substituted, for example, with an aryl group such as the (C6–C12) aryl group, which may be substituted, as described above, and examples thereof include, for example, an aralkyl group.

Specific examples thereof include, for example, a benzyl group, 2-phenylethyl group, 2-naphthylethyl group, diphenylmethyl group and the like.

Examples of the aryloxy group which may be substituted, represented by Ar group, include, for example, the same aryloxy groups as described above, and specific examples thereof include, for example, a phenoxy group, tolyloxy group, xylyloxy group, naphthyloxy group, biphenyloxy group or the like.

Examples of the arylene, heteroarylene or alkylene group, which may be substituted formed by Ar groups on the same phosphorus atom include, for example, naphthylene, phenanthrylene, phenanthridinylene, bicyclo[4,4,0] decylene, and the like.

Specific examples of the chiral phosphine compound of formula (1) include, for example,
N,O-bis(diphenylphosphino)-α,α-dimethyl (azetidine-2-yl) methanol,
N,O-bis(diphenylphosphino)-α,α-diethyl (azetidine-2-yl) methanol,
N,O-bis(diphenylphosphino)-α,α-diisopropyl (azetidine-2-yl)methanol,
N,O-bis(diphenylphosphino)-α,α-dibenzyl (azetidine-2-yl) methanol,
N,O-bis(diphenylphosphino)-α,α-diphenyl (azetidine-2-yl) methanol, and chiral phosphine compounds having an o-tolyl, 1-naphthyl, or cyclohexyl group in place of the phenyl group on the phosphrous atom respectively in the above described compounds.

The transition metal complex of the chiral phosphine compound formula (1) as defined above can be prepared, for example, from the chiral phospine compound of formula (1) and a transition metal compound.

The transition metal compound typically comprises a transition metal or its ion, and at least one or more chelating ligands. The chelating ligand may be neutral molecule or a charged ion and may possess a plurality of coordination sites.

Examples of the transition metal compound include, for example, a transition metal compound of formula (5):

$$[MY_pL_s]_t \qquad (5),$$

wherein M represents the transition metal as described above,

Y represents a hydrogen atom, a halogen atom, an acyloxy group, an alkoxyl group or a hydroxy group, L represents a ligand, p and s each represent an integer of 0 to 6, and t is an integer of 1 or 2.

In the definition above, p+s usually represents an integer of 2 to 8, depending upon the metal "M".

Examples of the transition metal compound include, for example,
chlorotris(triphenyl phosphine)rhodium (I),
cyclopentadienyl bis(triphenyl phosphine)rhodium (I),
bis(cyclooctadiene)diiodedi-rhodium (I),
rhodium triflate cyclooctadiene complex (Rh(COD)$_2$OTf),
chloro(1,5-cyclooctadiene)rhodium (I) dimmer ([RhCl (COD)]$_2$)
chloro(cyclopentadienyl)bis(triphenylphosphine)ruthenium (II),
chloro(pentamethylcyclopentadienyl) (1,3-bis(diphenyl phosphino)propane)ruthenium (II),
chloro(pentamethylcyclopentadienyl)(1,5-cyclooctadiene) ruthenium (II),
dichlorotris(triphenylphosphine)ruthenium (II),
chlorotris(triphenylphosphine)iridium (I),
pentamethylcyclopentadienylbis(ethylene)iridium (I),
chloro(1,5-cyclooctadiene)iridium (I) dimmer ([IrCl(COD)] $_2$)
(ethylene)bis(triphenyl phosphine)platinum (O),
trans-[chloro(ethyl)bis(triethyl phosphine)platinum (II)],
cis-[diethylbis(triethylphosphine)platinum (II)],
dichloro(norbornadiene)platinum (II) and
tetrakis(triphenylphosphine)platinum (O), and the like.

The complex that may be used in this invention are not limited to those described above.

The transition metal complex of a compound of formula (1) can be produced, for example, by the following method.

The chiral phosphine compound of formula (1) is usually dissolved in a solvent, and the above transition metal complex is added thereto. The resultant reaction solution is concentrated to produce the transition metal complex of a chiral phosphine compound of formula (1).

When the reaction product is obtained as precipitates, the solids may be isolated as such. The above operation is carried out usually in an inert gas atmosphere such as argon. The solvent used in such reaction is not particularly limited insofar as the reaction is not inhibited, and examples thereof include ethers such as tetrahydrofuran, diethyl ether etc., unsaturated hydrocarbons such as toluene, benzene etc., hydrocarbons such as hexane, cyclohexane etc., and halogenated hydrocarbons such as dichloromethane, chloroform, chlorobenzene etc. The solvent is more preferably ethers such as tetrahydrofuran, diethyl ether etc.

The transition metal complex of a chiral phosphine compound of formula (1) typically includes a transition metal complex of formula (6):

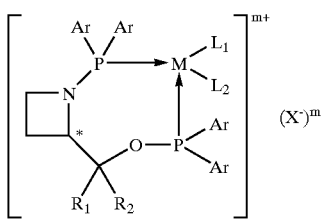

(6)

wherein $R_1$, $R_2$ and Ar represent the same as defined above,

M represents a transition metal,

X— represents a counterion, m is an integer of 0 to 4, $L_1$ and $L_2$ independently represent a ligand, or $L_1$ and $L_2$ are bonded to form a divalent single ligand, and

* represents an asymmetric carbon atom;

Examples of the transition metal represented by M are preferably rhodium, ruthenium, palladium, iridium and platinum. In particular, rhodium and ruthenium are preferably used in asymmetric reduction reaction of unsaturated organic compounds.

Examples of the counterion represented by X- include, preferably a halogen anion such as a fluorine ion, a chlorine ion, a bromine ion, or an iodine ion, perchlorate anion, hexafluorophosphate anion, tetrafluoroborate anion, trifluoromethylbenzenesulfonate anion, and trifluoromethanesulfonate anion and the like.

Any ligand, represented by $L_1$ and $L_2$, that can form a complex with the transition metal, by coordination thereof, may be used, and examples thereof include, for example, carbon monoxide, nitrogen monoxide, $NH_2$, a halogen atom such as chlorine, bromine etc., an olefinic ligand, an acetylenic ligand, an aromatic compound ligand, organic oxygen-containing compound ligands, organic sulfur-containing compound ligands, organic nitrogen-containing compound ligands and the like.

Examples of the olefinic ligand include, for example, ethylene, allyl, butadiene, cyclohexene, 1,3-cyclohexadiene, 1,5-cyclooctadiene, cyclooctatriene, norbornadiene, acrylate, methacrylate, cyclopentadienyl, pentamethyl cyclopentadienyl etc. Examples of the 5-memberred compound that may be used as a ligand include, for example, a 5-memberred compound of the following formula (7):

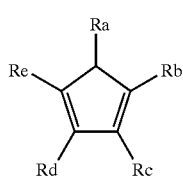

(7)

wherein Ra to Re are the same or different and independently represent a hydrogen atom, a halogen atom, a heteroaryl or aryl group, which may be substituted, an alkyl or alkenyl group, which may be substituted, or an alkoxy, aryloxy, alkoxycarbonyl or aryloxycarbonyl group, which may be substituted.

Examples of the halogen atom includes, a fluorine atom, a chlorine atom, a bromine atom, and an iodine atom.

The heteroaryl group and the aryl group which may be substituted, including the aryl groups of aryloxy group and aryloxycarbonyl groups above respectively mean the same heteroaryl and aryl groups as described for $R_1$ and $R_2$ groups above.

The alkyl group including alkyls of the alkoxy and alkoxycarbonyl means the same alkyl groups as described above for $R_1$ and $R_2$.

Examples of the aryl group include, for example, a phenyl group, naphthyl group, biphenyl group, furyl group, thienyl group and the like.

Examples of the alkoxyl group include, for example, a methoxy group, ethoxy group, n-propoxy group, t-butoxy group etc., the aryloxy group includes a phenoxy group and the like.

Examples of the alkoxycarbonyl group include, for example, a methoxycarbonyl group, ethoxycarbonyl group, t-butyloxycarbonyl group, benzyloxycarbonyl group etc and the like.

Examples of the aryloxycarbonyl group includes a phenyloxycarbonyl group and the like.

Examples of the alkenyl group, which may be substituted include, for example, a (C2–C6) linear, branched or cyclic alkenyl group such as a 2-methyl-1-propenyl group, 2-butenyl group, trans-β-styryl group, 3-phenyl-1-propenyl group, 1-cyclohexenyl group and the like.

The heteroaryl, aryl, aryloxy, or aryloxycarbonyl group, represented by Ra to Re, may be substituted with a halogen atom, an alkyl, alkoxy, aryloxy, arylthio, alkylthio, nitro, or hydroxy group.

The alkyl or alkenyl group, alkoxycarbonyl group, represented by Ra to Re, may be substituted with a halogen atom, an alkoxy, aryloxy, arylthio, alkylthio, nitro, or hyroxy group.

Examples of the aryloxy group include a phenoxy group. Examples of the alkyl group include, for example, a methyl group, ethyl group, isopropyl group, n-butyl group, t-butyl group, n-amyl group and n-hexyl group. Examples of the alkylthio group include, for example, n-propylthio group, t-butylthio group and the like.

Examples of the arylthio group include, for example, a phenylthio group and the like.

The acetylenic ligands include, e.g. acetylene, 1,2-dimethyl acetylene, 1,4-pentadiine, 1,2-diphenyl acetylene etc.

The aromatic compound that may be used as a ligand includes an aromatic compound of the following formula (8):

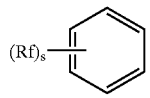

(8)

wherein Rf groups are the same or different and independently represent a halogen atom, a hydroxy group, a heteroaryl or aryl group, which may be substituted, an alkyl or alkenyl group, which may be substituted, or an alkoxy, aryloxy, alkoxycarbonyl or aryloxycarbonyl group, which may be substituted, and s represents an integer of 0 to 6.

The heteroaryl, aryl, alkyl, alkoxy, aryloxy, alkoxycarbonyl, and aryloxycarbonyl groups means the same groups as described for $R_1$ and $R_2$ above.

Examples of the alkenyl group, which may be substituted include, for example, a (C2–C6) alkenyl group such as vinyl group, propenyl, butenyl, pentenyl, hexenyl or the like.

Specific examples of the aromatic compound ligand include, for example, benzene, p-cymene, mesitylene, hexamethylbenzene, naphthalene, anthracene and the like.

The organic oxygen-containing compound ligands include e.g. acetate, benzoate, acetylacetonate etc.

The organic sulfur-containing compound ligands include e.g. dimethyl sulfoxide, dimethyl sulfide, thiophene, carbon disulfide, carbon sulfide, thiophenol and the like.

The organic nitrogen-containing compound ligands include e.g. acetonitrile, benzonitrile, t-butyl isocyanide, pyridine, 1,10-phenanthroline, 2,2'-bipyridyl and the like.

The chiral phosphine compound of formula (1) can be produced by a process comprising reacting the optically active azetidine alcohol compound of formula (2) with the phosphine of formula (3) usually in the presence of a base in an organic solvent.

Examples of the solvent include, for example, a hydrocarbon (e.g. toluene or the like), a halogenated hydrocarbon (e.g. dichloromethane or the like), and an ether (e.g. diethyl ether or the like).

The base is not particularly limited insofar as it does not inhibit the reaction, and preferable examples thereof include, for example, an organic amine such as triethylamine, tributylamine, pyridine, quinoline etc. When a base is used, the reaction can be promoted by adding 4-dimethylaminopyridine, 4-pyrrolidinopyridine etc.

The reaction temperature is usually $-20°$ C. to $150°$ C., particularly preferably about $0°$ C. to $50°$ C.

After completion of the reaction, a product can be obtained by removing the solvent from the reaction mixture through concentration etc, and the resulting product may be purified by filtration, and it may be further purified, if necessary, by column chromatography and/or recrystallization.

Examples of the phosphine of formula (3) includes, for example, chlorodiphenylphosphine, chlorodicyclohexylphosphine, chlorocyclohexylphenylphosphine, chloroditolylphosphine, chloro(methoxyphenyl)phosphine, chlorodi(3,5-dimethyl-4-methoxyphenyl)phosphine etc. Any amount of the phosphine can be used in the reaction, and it is usually used in an amount of 2 to 5 moles, preferably about 2 to 3 moles per mol of the optically active azetidine alcohol compound of formula (2).

The optically active azetidine alcohol of formula (2) as defined above can be obtained by a process comprising reacting the optically active azetidine-carboxylate of formula (9):

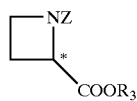
(9)

wherein $R_3$ represents a hydrogen atom or a hydrocarbon which may be substituted, Z represents a hydrogen atom or a protective group for an amino group, and

* represents an asymmetric carbon, with an organometallic alkylating agent, in one step or successive steps, followed by deprotection of Z when it is a protective group for an amino group, to give the chiral compound of formula (2).

Examples of the alkylating agent include, for example, a Grignard reagent of formula (10):

$$R_r MgX'$$ (10), wherein $R_r$ represents $R_1$ or $R_2$ as defined above,

X' represents a halogen atom.

Next a description will be made to the process for producing an optically active compound comprising asymmetrically reducing a prochiral unsaturated compound with hydrogen in the presence of the transition metal complex of a chiral phosphine compound of formula (1).

Examples of the prochiral unsaturated compound include, for example, a prochiral olefin compound, and examples thereof include an olefinic compound of formula (11):

$$(Z_1)(Z_2)C=C(Z_3)(Z_4)$$ (11)

wherein $Z_1$ and $Z_2$ are not the same and independently represent a hydrocarbyl group, which may be substituted, a group of formula (11a):

$$CO-R_4,$$ (11a)

wherein $R_4$ represents a hydroxy group, an alcohol residue group (e.g. a hydrocarbyl group, which may be substituted), a group of formula (11b):

$$NR_5(R_6)$$ (11b)

wherein $R_5$ represents a hydrocarbyl, acyl (e.g. an aryloyl or alkanoyl group such as acetyl group) or hydrocarbyloxycarbonyl group, which may be substituted, and $R_6$ independently represents the same group as $R_5$ or a hydrogen atom, and $Z_3$ and $Z_4$ are the same or different and independently represent a hydrogen atom or the same groups as defined for $Z_1$ and $Z_2$.

Examples of the hydrocarbyl group which may be substituted in the definitions of $Z_1$, $Z_2$, $R_4$, $R_5$, or $R_6$ include, for example, those exemplified in the definitions of $R_1$ or $R_2$. A substituent group that may be present on the hydrocarbyl group of $Z_1$, $Z_2$, $R_4$, $R_5$, or $R_6$ in addition to those defined above include, for example, a carboxylic acid ester or carboxylic amide group (e.g. —COOR' or —CONR'R", wherein R' and R" represent a linear, or branched alkyl group or an aryl group, or R' and R" are bonded at their terminals to form an alkylene group which may contain an oxygen atom, sulfur atom, a nitrogen atom or the like).

Examples of the optically active organic compound produced by the process include a compound of formula (12):

$$(Z_1)(Z_2)CH^*-CH(Z_3)(Z_4)$$ (12)

wherein $Z_1$ to $Z_4$ represent the same as defined above, and * represents an asymmetric carbon atom.

The amount of the transition metal complex of a chiral phosphine compound of formula (1) may be varied depending on reaction conditions and from an economical point of view, but said complex is used usually in the range of about $\frac{1}{10}$ to $\frac{1}{100,000}$ mole preferably about $\frac{1}{50}$ to $\frac{1}{10,000}$ mol per mol of the unsaturated prochiral organic compounds as the reaction substrate.

An additive may be added to improve yield and selectivity (optical purity of the product) in the hydrogenation reduction reaction of unsaturated prochiral organic unsaturated compounds as the reaction substrate. For example, an additive may be preferably used for iridium.

Examples of the additive include, for example, an amine compound such as benzyl amine, n-butylamine, triethylamine etc., iodides such as tetra-n-butyl ammonium iodide, bismuth triiodide, potassium iodide etc., and imide compounds such as phthalimide etc.

The amount of these additives is about 0.1 to 20 moles, preferably about 1 to 5 moles, per mole of the transition metal complex of a chiral phosphine compound of formula (1).

A solvent is usually used in this hydrogenation reduction reaction. The solvent used is preferably the one solubilizing the reaction starting materials and the catalyst system.

Examples of the solvent include, for example, aromatic solvents such as toluene, xylene etc., aliphatic solvents such as pentane, hexane etc., halogenated hydrocarbon solvents such as methylenechloride etc., ether solvents such as ether, tetrahydrofuran etc., alcohol solvents such as metanol, ethanol, 2-propanol, butanol, benzyl alcohol etc., polar solvents such as acetonitrile, N,N-dimethylformamide (DMF), N-methylpyrrolidone, pyridine, dimethylsulfoxide (DMSO) etc, and a mixture thereof.

Any amount of the solvent can be suitably used depending on the solubility of the reaction substrate and from an economical viewpoint.

The hydrogen pressure in this reaction is usually in the range of about 1 to 200 atms, preferably in the range of about 3 to 100 atms.

The reaction can be carried out usually at a temperature in the range of about =31 40 to 120° C., but from an economical viewpoint, the reaction can be carried out at about 15 to 100° C., more preferably at about 25 to 40° C.

The reaction in this invention can be carried out in a batch or continuous reaction system.

Effect of the Invention

The transition metal complex having a chiral phosphine compound of formula (1) in this invention is useful as a catalyst for the asymmetric reduction of unsaturated organic compounds in industrial-scale.

EXAMPLES

Hereinafter, this invention is described in more detail by reference to the Examples, which however are not intended to limit this invention.

Reference Example 1

10.0 g (45.6 mmol) of ethyl (S,S)-2-(N-α-methylbenzyl) azetidine-carboxylate was dissolved in 100 ml diethyl ether under an argon atmosphere, and 46 ml (137 mmol) of 3 M methyl magnesium bromide in diethyl ether was added dropwise thereto. After completion of the addition, the mixture was stirred for 2 hours under reflux. To the reaction mixture obtained after cooling was added 200 ml aqueous saturated ammonium chloride, and the aqueous water was extracted with diethyl ether, and the resultant organic layer was washed succively with water and aqueous saturated saline and then dried over anhydrous sodium sulfate. This organic layer was concentrated to give 9.24 g (S,S)-α,α-dimethyl-2-(N-α-methylbenzyl)azetidine-methanol (yield 92%) as yellow oil.

4.0 g (18.2 mmol) of (S,S)-α,α-dimethyl-2-(N-α-methylbenzyl)azetidine-methanol thus obtained was dissolved in a mixed solvent of 100 ml of methanol, 10 ml of water and 2 ml of acetic acid, then 350 mg of palladium hydroxide supported on activated carbon was added, and the mixture was reacted at room temperature for 10 hours in a hydrogen stream. The resultant reaction mixture was filtered through Celite, then the filtrate of reaction mixture was concentrated under reduced pressure, and the resultant residues were dissolved in 50 ml of 1 N hydrochloric acid and washed with diethyl ether. After washing, the residues was contacted with aqueous sodium hydroxide and extracted twice with 30 ml chloroform, and the resultant organic layer was washed with water and saturated aqueous saline, dried over anhydrous sodium sulfate and concentrated to give 1.55 g of (S)-α,α-dimethyl-2-azetidine-methanol (yield 74%) as a white solid. The melting point was 49 to 50° C.

Reference Example 2

(S)-α,α-Diethyl-2-azetidine-methanol was obtained as white solid in a similar manner as in Reference Example 1 except that ethyl magnesium bromide was used in place of methyl magnesium bromide. The melting point was 54 to 55° C.

Reference Example 3

(S)-α,α-Diisopropyl-2-azetidine-methanol was obtained as white solid in a similar manner as in Reference Example 1 except that isopropyl magnesium bromide was used in place of methyl magnesium bromide. 300 MHz NMR (CDCl$_3$, δ (ppm): 0.8–1.0 (12H, d, isopropyl CH3), 1.8–1.85 (2H, m, isopropyl CH), 1.85–2.0 (1H, m), 2.4–2.5 (1H, m), 3.0–3.1 (1H, m), 3.5–3.6 (1H, m), 4.2–4.3 (1H, t, —CHN—).

Reference Example 4

5.0 g (22.8 mmol) of methyl (S,S)-2-(N-α-methylbenzyl) azetidine-carboxylate was dissolved in 50 ml diethyl ether under an argon atmosphere, and 68.4 ml (68.4 mmol) of 1 M phethyl magnesium bromide in tetrahydrofuran was added dropwise thereto. After completion of the addition, the mixture was stirred for 2 hours under reflux. To the reaction mixture obtained after cooling was added 200 ml aqueous saturated ammonium chloride, and the aqueous layer was extracted with diethyl ether, and the separated organic layer was washed successively with water and aqueous saturated saline and then dried over anhydrous sodium sulfate. This organic layer was concentrated to give 10.0 g (S,S)-α,α-diphethyl-2-(N-α-methylbenzyl)azetidine-methanol (crude yield 128%) as yellow oil.

4.0 g (13.4 mmol) of the (S,S)-α,α-diphethyl-2-(N-αmethylbenzyl)azetidine-methanol thus obtained was dissolved in a mixed solvent of 100 ml of methanol, 10 ml of water and 2.5 ml of acetic acid, then 500 mg palladium hydroxide supported on activated carbon was added, and the mixture was reacted at room temperature for 10 hours under a hydrogen stream. The resultant reaction mixture was filtered through Celite, then the filtrate of the reaction mixture was concentrated under reduced pressure, and the resultant residues were contacted with 2M aqueous sodium hydroxide and extracted twice with 30 ml of chloroform, and the resultant organic layer was washed with water and saturated aqueous saline, dried over anhydrous sodium sulfate and concentrated to give 3.06 g of while crystals, which was further recrystallized twice with hexane to yield 2.0 of (S)-α,α-diphethyl-2-azetidine-methanol (yield 62%) as white crystals.

Example 1

200 mg (1.74 mmol) of (S)-α,α-dimethyl-2-azetidine-methanol obtained in Reference Example 1, 457 mg (4.5 mmol) of triethylamine and 42 mg (0.35 mmol) of 4-dimethylaminopyridine were dissolved in 5 ml anhydrous tetrahydrofuran in a nitrogen atmosphere, and a solution of 996 mg (4.5 mmol) chlorodiphenyl phosphine in 3 ml tetrahydrofuran was added dropwise thereto, and the mixture was reacted at room temperature for 19 hours. The resultant reaction mixture was diluted with diethyl ether to remove unnecessary materials, and then concentrated under reduced pressure. The resultant residues were purified by a column with silica gel and basic alumina, to give 679 mg (S)—N,O-bis(diphenylphosphino)-α,α-dimethyl-2-azetidine-methanol (yield 81%) as colorless oil. 300 MHz NMR (CDCl$_3$, δ (ppm): 1.4 (3H, s, CH3), 1.54 (3H, s, CH3), 1.9–2.0 (1H, m), 2.1–2.3 (1H, m), 2.9–3.1 (1H, m), 3.4–3.5 (1H, m), 4.0–4.1 1H, m, —CHN—), 7.2–7.6 (20H, m, phenyl).

Example 2

150 mg (0.31 mmol) (S)—N,O-bis(diphenylphosphino)-α,α-dimethyl-2-azetidine-methanol obtained in Example 1 was dissolved in 1 ml of anhydrous tetrahydrofuran under an argon atmosphere, and 121 mg (0.26 mmol) of rhodium triflate cyclooctadiene complex (Rh(COD)$_2$OTf) was added, and the resultant red solution was stirred for 1 hour. Thereafter, 5 ml anhydrous diethyl ether was added, whereby 154 mg of triflate salt of (S)-N,O-bis (diphenylphosphino)-α,α-dimethyl-2-azetidine-methanol/rhodium cyclooctadiene complex (yield 70%) was obtained as fine orange powder.

Example 3

300 mg (1.25 mmol) of (S)-α,α-diphenyl-2-azetidine-methanol obtained in Reference Example 4, 330 mg (3.25 mmol) of triethylamine and 42 mg (0.35 mmol) of 4-dimethylaminopyridine were dissolved in 5 ml anhydrous tetrahydrofuran under nitrogen atmosphere, and a solution of 720 mg (3.25 mmol) of chlorodiphenylphosphine in 3 ml tetrahydrofuran was added dropwise thereto, and the mixture was reacted at room temperature for 72 hours. The resultant reaction mixture was diluted with diethyl ether and filtered by silica gel and basic alumina to give a filtrate, which was then concentrated under reduced pressure. The resultant residues were purified by a column with silica gel and basic alumina to give 581 mg (S)-N,O-bis (diphenylphosphino)-α,α-diphenyl-2-azetidine-methanol (yield 77%) as a white solid. 300 MHz NMR (CDCl$_3$, δ (ppm): 1.9–2.1 (1H, m), 2.2–2.4 (1H, m), 2.8–3.0 (2H, m), 5.1–5.2 (1H, m), 7.1–7.6 (30H, m, phenyl).

Example 4

150 mg (0.25 mmol) of (S)-N,O-bis(diphenylphosphino)-α,α-diphenyl-2-azetidine-methanol obtained in Example 3 was dissolved in 1 ml anhydrous tetrahydrofuran under argon atmosphere, and 96 mg (0.21 mmol) of rhodium triflate cyclooctadiene complex (Rh(COD)$_2$OTf) was added thereto, and the resultant reddish solution was stirred for 1 hour. Thereafter, 5 ml anhydrous diethyl ether was added and concentrated gently to give a residue. Anhydrous ether was added to the residue and oily material appeared on the surface was removed, and further addition of anhydrous ether gave an orange colored fine power was obtained. Solvent was removed therefrom and the solid material was dried under reduced pressure to give 60 mg of triflate salt of (S)-N,O-bis(diphenylphosphino)-α,α-diphenyl-2-azetidine-methanol/rhodium cyclooctadiene complex (yield 30%).

Example 5

100 mg of α-acetylamino-4-chlorostyrene and 2.2 mg of the triflate salt of (S)-N,O-bis(diphenylphosphino)-α,α-dimethyl-2-azetidine-methanol/rhodium cyclooctadiene complex obtained in Example 2 were dissolved in 3 ml of isopropanol under an argon atmosphere. The mixture was reacted at a hydrogen pressure of 10 atm at 40° C. for 6 hours in an autoclave. After the reaction was finished, the reaction mixture was concentrated, and the residues were purified by silica gel chromatography, whereby the desired optically active N-acetyl-(4-chloro)-α-phenethylamine, 90 mg (yield 90%), was obtained. The optical purity of the product, which was analyzed by HPLC having an optically active stationary phase, was 71% ee.

Examples 6 to 13

Experiments were conducted in a similar manner as in Example 5 except that the reaction conditions: the reaction catalyst, the reaction substrate, the reaction solvent, and the reaction temperature as listed in Table 1 were employed.

TABLE 1

| Ex. | Reaction Catalyst | Prochiral olefin | Solvent Temp | conv. (%) e.e. (%) |
|---|---|---|---|---|
| 6 | 1 | Ph-CH=C(NHAc)CO$_2$Me | MeOH Room Temperature | 100/84(S) |
| 7 | 2 | Ph-CH=C(NHAc)CO$_2$Me | MeOH Room Temperature | 100/89(R) |
| 8 | 1 | Naphthyl-CH=C(NHAc)CO$_2$Me | MeOH Room Temperature | 100/83(S) |

TABLE 1-continued
| Ex. | Reaction Catalyst | Prochiral olefin | Solvent Temp | conv. (%) e.e. (%) |
|---|---|---|---|---|
| 9 | 2 | 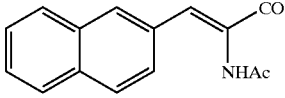 | MeOH Room Temperature | 100/88(R) |
| 10 | 2 | 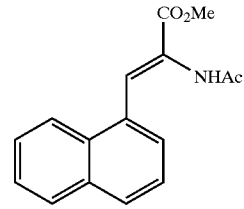 | MeOH Room Temperature | 100/84(R) |
| 11 | 1 | 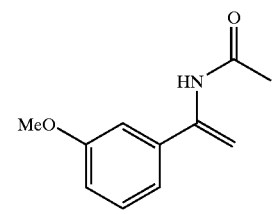 | i-PrOH 40° C. | 100/80 |
| 12 | 1 | 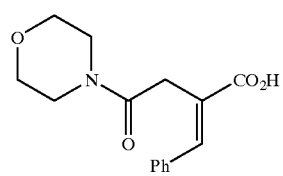 | MeOH Room Temperature | 100/80 |
| 13 | 1 | 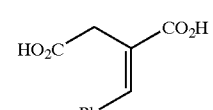 | MeOH 0° C. | 100/84 |
Reaction Catalyst:
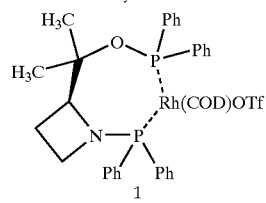
1
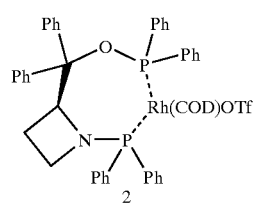
2
"COD" means cyclooctadiene.
"Tf" means trifluoromethanesulfonate.

What is claimed is:

1. A chiral phosphine compound of formula (1):

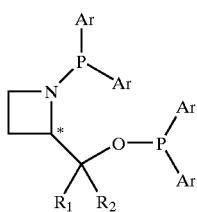

wherein $R_1$ and $R_2$ independently represent an aryl or heteroaryl group, which may be substituted, a saturated hydrocarbon group, which may be substituted, and Ar group independently represents a heteroaryl group, which may be substituted, an aryloxy group, which may be substituted, or Ar groups on the same phosphorous atom are bonded to form an arylene, heteroarylene or alkylene group, which may be substituted, and

* represents an asymmetric carbon atom.

2. A process for producing a chiral phosphine compound of formula (1):

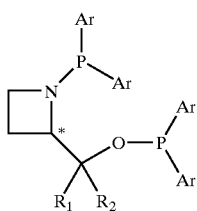

wherein $R_1$ and $R_2$ independently represent an aryl or heteroaryl group, which may be substituted, a saturated hydrocarbon group, which may be substituted, and Ar group independently represents heteroaryl group, which may be substituted, an aryloxy group, which may be substituted, or Ar groups on the same phosphorus atom are bonded to form an arylene, heteroarylene or alkylene group, which may be substituted, and

* represents an asymmetric carbon atom, which comprises reacting an optically active azetidine alcohol compound of formula (2):

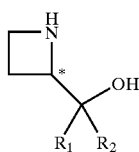

wherein $R_1$, $R_2$ and * represent the same as defined above, with a phosphine of formula (3):

$$XPAr_2 \qquad (3)$$

wherein X represents a halogen atom, and Ar represents the same as defined above.

* * * * *